United States Patent [19]

Sabin

[11] Patent Number: 5,217,959
[45] Date of Patent: Jun. 8, 1993

[54] METHOD OF TREATING MULTIPLE SCLEROSIS WITH PHYTIC ACID

[76] Inventor: Robert Sabin, Goosedown Estate, Box 332, Mill Neck, Long Island, N.Y. 11765

[21] Appl. No.: 578,652

[22] Filed: Sep. 6, 1990

[51] Int. Cl.⁵ .............................................. A61K 31/70
[52] U.S. Cl. ...................................................... 514/23
[58] Field of Search ......................................... 514/23

[56] References Cited

PUBLICATIONS

Young et al., Journal Neurol. Psychiatry, Mar. 49(3) (1986) pp. 265-272.
*Journal of Applied Nutrition*, vol. 42, No. 1, 1990, R. Jariwalla, "Lowering of Serum Cholesterol and Triglycerides and Modulation of Divalent Cations by Dietary Phytate".
*The Lancet*, vol. 336, No. 8706, Jul. 7, 1990, R. Swank, "Effect of Low Saturated Fat Diet in Early and Late Cases of Multiple Sclerosis" pp. 37-39.
*AMA Family Med. Guide*, R. Kunz, "Multiple Sclerosis", pp. 292-293.
*A Good Health Guide*, J. Bland, vol. 1-*Mayo Clinic Nutrition Letter* Apr. 1990, "Triglycerides".

*Primary Examiner*—S. J. Friedman

[57] ABSTRACT

A method is provided for treating multiple sclerosis by administering to a subject afflicted with that disease a symptom-alleviating amount of a compound selected from the group consisting of phytic acid, mixed counterion phytate salt, an isomer or hydrolysate of phytic acid or mixed counterion phytate salt, a mixture of any combination thereof, or with one or more dephosphorylating enzymes. The preferred method of administration is by oral dosages of about ½ to 3 grams/kilogram bodyweight per day.

10 Claims, No Drawings

METHOD OF TREATING MULTIPLE SCLEROSIS WITH PHYTIC ACID

The present invention relates to a novel method of treating multiple sclerosis and more precisely, to a method of treatment utilizing biologically active phytic acid and lower inositol phosphates derived from the hydrolysis of phytic acid in vivo.

BACKGROUND OF THE INVENTION

Phytic acid, generally accepted as having the structure myo-inositol-hexakis (dihydrogen phosphate), is a major component of plant seeds, constituting 1-3% by weight of many cereals and oil seeds. Most wheat brans contain between 4 and 5% phytic acid. Phytic acid may be prepared in pure form from various plant sources, such as wheat, corn, soybeans, sesame seeds, peanuts, lima beans, barley, oats, wild rice and sunflower seeds. It can be extracted with dilute hydrochloric acid at room temperature, precipitated with various reagents including ferric chloride, bicarbonates, potassium hydroxide, sodium hydroxide, ammonium hydroxide, calcium hydroxide, magnesium hydroxide or alcohol. It is then further purified by conventional chemical techniques.

When one or more of the acidic protons of the phosphate groups in phytic acid are replaced by a counterion, the compound is usually referred to as a phytate salt. The name phytin is used for the calcium-magnesium salt of phytate derived from plant seeds (a discontinued product of Ciba-Geigy). The present invention includes the use not only of phytic acid and phytate salts, but also various isomeric forms of phytic acid and phytate salts. While the Anderson structure for myo-inositol hexakis dihydrogen phosphate is the accepted structure for phytic acid, the present invention covers other isomers which have been previously described in the literature. These isomers include the cis, epi, allo, muco, neo, D-chiro, L-chiro, and scyllo configurations.

Also, while phytic acid contains six phosphate groups, when introduced into the digestive tract of an animal, one or more of the phosphate groups may be hydrolyzed by the action of the digestive acids and enzymes. Therefore, the present invention includes the use of hydrolysates of phytic acid and phytate salts wherein one or more of the phosphate groups have been removed.

The main uses of phytic acid include use as a food additive for preservation of foods. Studies on the use of phytic acid as a food additive show that ingestion of large doses of phytic acid elicits no physiological discomfort or symptoms of any toxicological action in humans. See Starkenstein, *Biochem. Z.* 30: 56 (1911). Phytic acid and its metabolites are thus not believed to be toxic or highly reactive.

Medical applications of phytic acid include use as an imaging agent for organ scintography, an X-ray enhancement contrasting agent and use to reduce gastric secretion for treatment of gastritis, gastroduodenitis, gastric duodenal ulcers and diarrhea. It has been suggested as an antidote for toxic metal absorption, for therapeutic use in the prevention and dilution of calcium deposits associated with various diseases and for reducing calcium concentration in urine (thus checking the formation of renal calculi). Other uses include as a preventive agent against severe poisoning with pressurized oxygen and preventing thirst during exercise. It has been used as a counterion in salts with various orally administered antibiotics to improve taste.

Klevay has reported that a diet containing added sodium phytate content produced hypocholesterolemia in normal rats. See *Nutr. Rep. Int.*, 15:587 (1977).

Phytic acid has also been suggested to reduce the incidence of dental caries, and has been utilized in dentifrices, mouth rinses, dental cements, cleaning agents for dentures and for removing nicotine tar from teeth.

Industrial uses of phytic acid include use as a corrosion inhibitor on metals, a rust remover and an additive to lubricating greases. Other miscellaneous uses of phytic acid include oral administration to treat acne, to improve skin color, blood circulation and fingernail growth; and as an additive in cosmetics for anti-dandruff hair lotions and skin care lotions. One potential agricultural use of phytic acid is to inhibit aflatoxin production by *Aspergillus parasiticus*. It is also useful as an additive to a fermentation medium containing *Micromonospora sagamiensis* in the fermentative production of antibiotics. Similarly, phytic acid may be used as a growth-promoting factor in the fermentation medium for the cultivation of yeast for feed.

For further discussions of industrial applications of phytic acid, see Graf, *JAOCS* 60, 1861-1867 (1983).

Although the above description indicates the broad scope of potential uses of phytic acid, there is not believed to be any suggestion in the prior art that phytic acid is useful for the treatment of multiple sclerosis.

Many nerve tracks or pathways in the central nervous system, which includes the brain and spinal cord, are laminated in a protective covering called myelin. This myelin lamination supplies nutrients to the nerves within it and also accelerates up the passage of electrical impulses along the nerves. If any of these sheaths become inflamed, swollen or demyelinated, the flow of messages within the nerves is blocked and/or distorted. Furthermore, messages are not received correctly or go to the wrong area. If two or more parts of the central nervous system are involved the disease known as multiple sclerosis is diagnosed. Any part of the brain or spinal cord which contains myelin covered nerves can be affected. This disease afflicts between 250,000 to 500,000 Americans.

There is currently no cure or prospect of a cure for multiple sclerosis. Current pharmacological intervention is solely aimed at relieving specific symptoms of acute or chronic attacks such as muscle spasms and certain hormones to reduce severity and duration of acute attacks. Steroid injections and B complex vitamin supplements are utilized. Moreover, mechanical intervention is utilized to treat urinary incontinence resulting from multiple sclerosis by means of a catheter inserted in the bladder. Moreover, physical therapy, psychotherapy and counseling and continued medical reevaluation are also employed in the treatment of multiple sclerosis. Multiple sclerosis follows vastly different courses in different people, some immediately crippled overnight, remitting and relapsing. Others become progressively weaker over many years. Therefore, any pharmacological intervention or nutrient supplement that would slow down or reverse or ameliorate the progressive deterioration of a multiple sclerosis patient would be a great contribution for the patient, would relieve untold pain and suffering for the patient, their family and society. Briefly, several of the current scientific theories of the etiology of multiple sclerosis are virus attacks, whereby certain slow acting viruses attack in the myelin sheaths causing swelling, inflammation and demyelination.

Immune Reaction

Many scientists consider multiple sclerosis an autoimmune disease, whereby the body's immune system attacks its own tissues by mistake. Many scientists believe that multiple sclerosis might involve a combination of virus and immune reactions, whereby the immune system cannot distinguish between virus infected cells and virus free cells, whereby, the immune system attacks both whole cells and viral infected cells. Other scientists postulate that free radical formation a normal metabolic process becomes excessive resulting in damage to the myelin covered nerve sheaths. Multiple sclerosis remains a disease of unknown etiology.

Of primary importance is that inositol, the ultimate product of phytic acid metabolism in vivo is inositol. Inositol has recently been found to function as a potent cell growth factor because it stimulates the production of complex phospholipids which are used by the body for the production of myelinated nerve material. A demonstration of a pharmacological demonstration is peripheral neurological complications of diabetes which include pain in the hands and feet. Tingling sensation and numbness of fingers and toes, with reduced nerve conduction velocity can be treated by administering therapeutic doses of inositol. Furthermore, Salaway in a clinical trial used one gram of inositol to increase action potentials of nerves and nerve conduction.

Since phytic acid strongly stimulates the production of complex phospholipids used by the body for the manufacture of myelinated nerve material the stimulation of the production of this myelinated nerve material will enable the body to regenerate, renew and repair and thus withstand or ameliorate the onslaught of inflammation, swelling and demyelination occurring in multiple sclerosis. Furthermore, this damage to myelinated nerve material may be caused by a deficiency or abnormality of the fatty substance, which makes up myelin.

Inositol has recently been found to function as a cell growth factor, because it stimulates the manufacture in the body of complex phospholipids. These phospholipids are a class of fats used in the body for the manufacture of myelinated nerve sheaths. Abnormal low amounts of inositol can reduce nerve growth and regeneration.

The most important clinical manifestation of this observation is the recent work which has indicated that peripheral neurological complications of diabetes which involve pain in the hands and feet, tingling sensation, and numbness of the fingers and toes with reduced nerve conduction velocity can be treated by administering large therapeutic doses of inositol as a supplement. This condition of peripheral neuritis is responsive to myo-inositol supplementation at levels of 1000 to 3000 mg per day. The average American 2500 kilocalorie diet contains 900 mg of inositol, and most individuals claim that this amount is more than adequate to meet the daily needs. In diabetics, with peripheral neuritis, the level of inositol in the average diet is not high enough to be in the effective therapy range. When there is an increase from 770 to 1640 mg per day of inositol, there has been found a significant improvement in the sensory neurons of diabetics with neuropathy. The level of 1600 mg can be achieved by careful selection of certain foods for the diet, but in general it is very difficult to achieve from dietary sources alone and an inositol supplement may be required. Salaway, J. G., et al., 1978 *Lancet,* Dec. 16, pp. 1282-84, in a clinical trial used 1000 mg per day of inositol as a tablet in diabetics to increase action potentials of nerves and nerve conduction velocity and has successfully managed peripheral neuropathy in diabetics.

Accordingly, it is an object of the present invention to provide a method for treating multiple sclerosis levels comprising the step of treating a multiple sclerosis patient with phytic acid, phytate mixed counterion salts, and isomers or hydrolysates thereof.

This and other objects will be made apparent by the following description of the preferred embodiments and appended claims.

SUMMARY OF THE INVENTION

The present invention provides a method treating multiple sclerosis comprising the step of administering to a subject afflicted with multiple sclerosis an effective symptom-alleviating dose of a compound selected from the group consisting of phytic acid, a mixed counterion phytate salt, an isomer or hydrolysate of phytic acid or mixed counterion phytate salt, or a mixture of any combination thereof. The preferred method of administration is by the oral route.

DESCRIPTION OF THE PREFERRED EMBODIMENTS

The method according to the present invention comprises treating a subject afflicted with multiple sclerosis with a composition in which the active ingredient is phytic acid, a mixed counterion phytate salt, or an isomer or hydrolysate of phytic acid or mixed counterion phytate salt. By the term isomer as used herein, it is intended to include the various conformations of phytic acid, as described hereinabove, and the corresponding conformations of phytate salts. The term salts is broadly intended to cover any of the various salts formed by the replacement of two or more of the available acidic protons of the phosphate groups with a counterion. The counterions may be any combination of pharmaceutically acceptable counterions such as sodium, magnesium, potassium, zinc, ferric, ferrous, and the like, including organic counterions such as quaternary ammonium ions and ions of organic bases.

The present invention also includes the hydrolysates of phytic acid and phytate salts wherein one or more of the phosphate groups have been removed. Once administered into the digestive tract or bloodstream of the subject, the phytic acid or phytate salt may be hydrolyzed by digestive, blood or cellular enzymes, thereby removing one or more of the phosphate groups on the cyclohexane ring. However, it is contemplated to be within the scope of the invention that these hydrolysates of phytic acid and phytate salts may also be administered directly to the subject and therefore are within the scope of the present invention.

The hydrolysates of phytic acid and phytate salts may be prepared by partial acid or basic hydrolysis or by hydrolysis using enzymes prior to preparation of dosage forms for administration. Preferably, the hydrolysates will be made in vivo by coadministering with phytic acid or phytate salt an enzyme which hydrolyzes phosphate groups, such as extracellular phytase (E.C. 3.1.3.8) from *Aspergillus ficuum* NRRL 3135, 6-phytase (E.C. 3.1.3.26), or other acid phosphatase or combination of enzymes.

The phytic acid or phytate salt may be absorbed into or adsorbed onto a solid carrier to facilitate pharmaceutical administration. For example, phytic acid may be formulated into a starch powder by spray drying or vacuum drying an aqueous mixture of phytic acid and dextrin.

The preferred compositions for administration, particularly in oral dosage form, are the mixed metal ion phytate salts or mixtures thereof, which may be prepared from commercially and readily available sodium phytate by initially removing the sodium using ion exchange chromatography on a suitable resin, such as Dowex beads. The free phytic acid may then be treated with appropriate bases to convert to the mixed metal ion phytate salts. The preferred salt is the phytic acid monopotassium phytate salt, $C_6H_{17}O_{24}P_6K$; MW 689.1 (white powder; forms clear, colorless solution in $H_2O$; solubility 50 mg/($H_2O$)).

The preferred method of administration of the compositions according to the present invention is through oral administration in liquid or tablet form. As described hereinabove, the compositions may be administered as pharmaceutically acceptable salts such as salts with alkali metal cations (sodium, potassium, lithium), ammonium salts and salts with organic bases such as piperidine, triethanolamine, diethylaminoethylamine salts, and the like.

In addition to the active ingredients, the composition may also contain an effective proportion, usually from 0.001 to 0.1% weight by volume, of a pharmaceutically acceptable preservative or sterilizing agent such as cetyl pyridinium chloride, tetradecyltrimethyl ammonium bromide (commercially known as Centramide), benzyl dimethyl [2-(2-)p-(1,1,3,3-tetramethylbutyl)) phenoxy) ethoxy] ammonium chloride (known commercially as Benzethonium Chloride) and myristyl-gamma-picolinium chloride.

The pharmaceutical composition may also contain conventional excipients, sodium chloride, dextrose, mannitol, and buffers such as sodium dihydrogen ortho phosphate, disodium hydrogen phosphate, sodium citrate/citric acid, and boric acid/sodium borate. The proportion and concentration of excipients and buffers may be varied within fairly wide ranges, providing the resulting solution is stable and nonirritating when administered. The preferred method of administration is by oral administration as a solid compound. The composition may be prepared in the conventional manner as tablets, pills or powders, using conventional carriers.

The dosage to be administered will vary with the severity of the symptoms of multiple sclerosis in the subject. However, in general, particularly for oral administration, from ½ to 3 grams of phytic acid (or equivalent phytate salt, isomer or hydrolysate) per kilogram of body weight in the diet per day will usually be effective. Frequency of dosage administration may, of course, be varied as needed and as discretionarily required by the attending physician.

For oral administration, in a preferred embodiment, the active ingredient of the composition will also contain an enzyme such as 3-phytase (EC 3.1.3.8), 6-phytase (EC 3.1.3.26), an acid phosphatase or combination of enzymes which, when exposed to the digestive tract, will assist in hydrolyzing one or more of the phosphate groups from the active ingredient. Since phytic acid or phytate salts are not naturally present in animals, the digestive enzymes in animals are believed to be insufficient to completely hydrolyze the phosphate groups. Therefore, to enhance the hydrolysis of the phosphate groups in an animal or man, it is preferred that the active ingredient be administered with one or more of the aforementioned enzymes, with the preferred enzyme being 3-phytase (EC 3.1.3.8) derived from known fermentation protocol, such as that described in Shieh, C. R. and J. N. Ware, *Applied Microbiol.* 16:1348 (1968).

What is claimed is:

1. A method of, treating multiple sclerosis comprising orally administering to a subject afflicted with multiple sclerosis an effective symptom-alleviating amount of a compound selected from the group consisting of phytic acid, a mixed counterion phytate salt, an isomer or hydrolysate of phytic acid or a mixed counterion phytate salt, or a mixture of any combination thereof.

2. A method according to claim 1 wherein said phytate salt comprises a monopotassium salt.

3. A method according to claim 2 wherein said monopotassium salt is characterized by the empirical formula $C_6H_{17}O_{24}P_6K$ molecular weight 689.1.

4. A method according to claim 1 wherein said phytic acid, salt, isomer, hydrolysate or mixture is absorbed into a pharmaceutically acceptable carrier.

5. A method according to claim 1 wherein said isomers of phytic acid or phytate salt comprise the hexakisphosphate myo-inositol, scyllo-inositol, D-chiro-inositol, L-chiro-inositol, neo-inositol and muco-inositol conformations.

6. A method according to claim 5 wherein said isomer of phytic acid or phytate salt is the hexakisphosphate myo-inositol conformation.

7. A method according to claim 1 wherein said hydrolysate of phytic acid or phytate salt comprises the pentakisphosphate, tetrakisphosphate, triphosphate, diphosphate, monophosphate or completely dephosphorylated hydrolysate.

8. A method according to claim 1 wherein said compound is administered orally in combination with a dephosphorylating enzyme.

9. A method according to claim 8 wherein said enzyme comprises 3-phytase, 6-phytase, acid phosphatase, or mixtures of any combination thereof.

10. A method according to claim 9 wherein said enzyme is 3-phytase EC 3.1.3.8.

* * * * *

UNITED STATES PATENT AND TRADEMARK OFFICE
CERTIFICATE OF CORRECTION

PATENT NO. : 5,217,959
DATED : June 8, 1993
INVENTOR(S) : Robert Sabin

It is certified that error appears in the above-indentified patent and that said Letters Patent is hereby corrected as shown below:

Column 5, line 40, after "excipients," add --e.g.--

Signed and Sealed this

Twenty-second Day of February, 1994

Attest:

BRUCE LEHMAN

Attesting Officer     Commissioner of Patents and Trademarks